United States Patent [19]
Scholz et al.

[11] Patent Number: 5,370,927
[45] Date of Patent: Dec. 6, 1994

[54] WET COMPACTING OF FABRICS FOR ORTHOPEDIC CASTING TAPES

[75] Inventors: Matthew T. Scholz, Woodbury; Jacquelyn A. Schmidt, St. Paul, both of Minn.

[73] Assignee: Minnesota Mining and Manufacturing Company, St. Paul, Minn.

[21] Appl. No.: 142,573

[22] Filed: Oct. 25, 1993

[51] Int. Cl.$^5$ .............................. B32B 7/00
[52] U.S. Cl. ......................... 428/254; 427/2.1; 427/322; 427/346; 427/389.8; 427/407.3; 427/2.31; 428/253; 428/266; 428/268
[58] Field of Search ............... 428/253, 254, 902, 266, 428/268; 602/3, 6, 8, 41, 44; 427/2, 322, 346, 389.8, 407.3

[56] References Cited

U.S. PATENT DOCUMENTS

| | | | |
|---|---|---|---|
| 2,765,513 | 10/1956 | Walton | 26/18.6 |
| 3,077,655 | 2/1963 | Runton | 26/18.5 |
| 3,421,501 | 1/1969 | Beightol | 128/90 |
| 3,630,194 | 12/1971 | Boardman | 128/90 |
| 3,686,725 | 8/1972 | Nisbet et al. | 28/74 R |
| 3,787,272 | 1/1974 | Nisbet et al. | 161/89 |
| 3,793,686 | 2/1974 | Nisbet et al. | 28/75 R |
| 3,837,338 | 9/1974 | Chesky et al. | 128/156 |
| 3,908,644 | 9/1975 | Neinart et al. | 128/90 |
| 3,932,526 | 1/1976 | Koshar | 260/607 A |
| 3,972,323 | 8/1976 | Boricheski | 128/91 R |
| 4,041,581 | 8/1977 | Diggle, Jr. | 26/18.6 |
| 4,131,114 | 12/1978 | Kirkpatrick et al. | 128/90 |
| 4,134,397 | 1/1979 | Gianakakos et al. | 128/90 |
| 4,376,438 | 3/1983 | Straube et al. | 128/90 |
| 4,411,262 | 10/1983 | von Bonin et al. | 128/90 |
| 4,441,262 | 4/1984 | Gazzoni | 34/57 D |
| 4,443,680 | 2/1984 | Yoon | 128/90 |
| 4,473,671 | 9/1984 | Green | 523/105 |
| 4,502,479 | 3/1985 | Garwood et al. | 128/90 |
| 4,609,578 | 9/1986 | Reed | 428/253 |
| 4,667,661 | 5/1987 | Scholz et al. | 428/254 |
| 4,668,563 | 5/1987 | Buese et al. | 428/230 |
| 4,704,113 | 11/1987 | Schoots | 604/379 |
| 4,705,840 | 11/1987 | Buckanin | 528/53 |
| 4,745,912 | 5/1988 | McMurray | 428/254 |
| 4,745,912 | 5/1988 | McMurray | 128/90 |
| 4,793,330 | 12/1988 | Honeycutt et al. | 428/254 |
| 4,800,872 | 1/1989 | Buese et al. | 128/90 |
| 4,841,958 | 6/1989 | Ersfeld et al. | 128/90 |
| 4,940,047 | 7/1990 | Richter et al. | 128/90 |
| 4,947,839 | 8/1990 | Clark et al. | 128/90 |
| 4,984,566 | 1/1991 | Sekine et al. | 128/90 |
| 5,014,403 | 5/1991 | Buese | 28/170 |
| 5,027,804 | 7/1991 | Forsyth et al. | 128/90 |
| 5,052,380 | 10/1991 | Polta | 428/254 |
| 5,060,349 | 10/1991 | Walton et al. | 26/18.6 |
| 5,061,555 | 10/1991 | Edenbaum et al. | 428/254 |
| 5,088,484 | 2/1992 | Freeman et al. | 128/89 R |
| 5,169,698 | 12/1992 | Behjati et al. | 428/68 |
| 5,180,632 | 1/1993 | Edenbaum et al. | 428/254 |
| 5,256,134 | 10/1993 | Ingham | 602/8 |
| 5,273,802 | 12/1993 | Scholz et al. | 428/254 |

FOREIGN PATENT DOCUMENTS

0407056A2  1/1991  European Pat. Off.

*Primary Examiner*—James J. Bell
*Attorney, Agent, or Firm*—Gary L. Griswold; Walter N. Kirn; F. Andrew Ubel

[57] ABSTRACT

The present invention provides an article, comprising: a fabric sheet which has been compacted using a heat shrink yarn; and a curable or hardenable resin coated onto the fabric sheet. The present invention involves compacting a fabric sheet to impart stretchability and conformability to the fabric while minimizing undesirable recovery forces. Suitable fabrics for compacting are fabrics which comprise fiberglass fibers which are capable of first being compacted and then being set or annealed in the compacted state. The article may be in the form of an orthopedic bandage and may optionally contain a microfiber filler associated with the resin.

21 Claims, 1 Drawing Sheet

WET COMPACTING OF FABRICS FOR ORTHOPEDIC CASTING TAPES

FIELD OF THE INVENTION

This invention relates to sheet materials coated with a curable or hardenable polymeric resin. More particularly, this invention relates to a curable or hardenable resin coated sheet material useful in preparing an orthopedic bandage.

BACKGROUND OF THE INVENTION

Many different orthopedic casting materials have been developed for use in the immobilization of broken or otherwise injured body limbs. Some of the first casting materials developed for this purpose involve the use of plaster of Paris bandages consisting of a mesh fabric (e.g., cotton gauze) with plaster incorporated into the openings and onto the surface of the mesh fabric.

Plaster of Paris casts, however, have a number of attendant disadvantages, including a low strength-to-weight ratio, resulting in a finished cast which is very heavy and bulky. Furthermore, plaster of Paris casts typically disintegrate in water, thus making it necessary to avoid bathing, showering, or other activities involving contact with water. In addition, plaster of Paris casts are not air permeable, thus do not allow for the circulation of air beneath the cast which greatly facilitates the evaporation and removal of moisture trapped between cast and skin. This often leads to skin maceration, irritation, or infection. Such disadvantages, as well as others, stimulated research in the orthopedic casting art for casting materials having improved properties over plaster of Paris.

A significant advancement in the art was achieved when polyisocyanate prepolymers were found to be useful in formulating a resin for orthopedic casting materials, as disclosed, for example, in U.S. Pat. No. 4,502,479 (Garwood et al.) and U.S. Pat. No. 4,441,262 (Von Bonin et al.). U.S. Pat. No. 4,502,479 sets forth an orthopedic casting material comprising a knit fabric which is made from a high modulus fiber (e.g., fiberglass) impregnated with a polyisocyanate prepolymer resin which will form a polyurea. Orthopedic casting materials made in accordance with U.S. Pat. No. 4,502,479 provide significant advancement over the plaster of Paris orthopedic casts, including a higher strength-to-weight ratio and greater air permeability. However, such orthopedic casting materials tend not to permit tactile manipulation or palpation of the fine bone structure beneath the cast to the extent possible when applying a plaster of Paris cast. In this regard, knit fiberglass materials are not as compressible as plaster, and tend to mask the fine structure of the bone as the cast is applied, e.g., the care provider may be limited in "feeling" the bone during reduction of the fracture.

Fiberglass backings have further disadvantages. For example, fiberglass backings are comprised of fibers which have essentially no elongation. Because the fiber elongation is essentially nil, glass fabrics do not stretch unless they are constructed with very loose loops which can deform upon application of tension, thereby providing stretching of the fabric. Knitting with loosely formed chain stitches imparts extensibility by virtue of its system of interlocking knots and loose loops.

To a greater extent than most knitted fabrics, fiberglass knits tend to curl or fray at a cut edge as the yarns are severed and adjacent loops unravel. Fraying and raveling produce unsightly ends and, in the case of an orthopedic cast, frayed ends may interfere with the formation of a smooth cast, and loose, frayed ends may be sharp and irritating after the resin thereon has cured. Accordingly, frayed edges are considered a distinct disadvantage in orthopedic casting tapes. Stretchy fiberglass fabrics which resist fraying are disclosed in U.S. Pat. No. 4,609,578 (Reed), the disclosure of which is incorporated by reference for its teaching of heat-setting. Thus, it is well known that fraying of fiberglass knits at cut edges can be reduced by passing the fabric through a heat cycle which sets the yarns giving them new three-dimensional configurations based on their positions in the knit. When a fiberglass fabric which has been heat-set is cut, them is minimal fraying and when a segment of yarn is removed from the heat-set fabric and allowed to relax, it curls into the crimped shape in which it was held in the knit. Accordingly, at the site of a cut, the severed yarns have a tendency to remain in their looped or knotted configuration rather than to spring loose and cause fraying.

In processing extensible fiberglass fabrics according to U.S. Pat. No. 4,609,578 (Reed), a length of fabric is heat-set with essentially no tension. The fabric is often wound onto a cylindrical core so large batches can be processed at one time in a single oven. Care must be taken to avoid applying undue tension to the fabric during wind-up on the knitter which would distort the knots and loops. To prevent applying tension to the fabric during winding, the winding operation is preferably performed with a sag in the fabric as it is wound on the core.

Alternatively, U.S. Pat. No. 5,014,403 (Buese) describes a method of making a stretchable orthopedic fiberglass casting tape by knitting an elastic yarn under tension into the fiberglass fabric in the length direction, releasing the tension from the elastic yarn to compact the fabric and removing the elastic yarn from the fabric. The resulting fabric must then be collected under low tension in order to preserve the compact form. Likewise, any subsequent heat setting must also be performed under low tension. However, to avoid exceeding this low tension is difficult and as a result substantial amounts of the compaction imparted by the elastomeric yarn may be lost during subsequent processes. The elastic yarn is removed by a combustion process which may cause localized areas of high temperature which may degrade the fiberglass yarns. The physical properties of glass fibers are adversely affected when subjected to temperatures in excess of about 540° C. Heating fiberglass fabrics to temperatures above about 540° C. should be avoided, as subjecting the fiberglass to temperatures of greater than about 540° C. can weaken the fiberglass yarns in the fabric, which may result in reduced strength of casts made from such fabrics.

Copending U.S. patent application: "Compacted Fabrics for Orthopedic Casting Tapes"—Ser. No. 08/141,830, filed on even date herewith by the assignee of the present invention, discloses an article comprising a fabric sheet (e.g., fiberglass) which has been compacted using a heat shrink yarn. The incorporation of the additional heat shrink yarn(s) into the knit structure requires an additional bar on the knitter and the attendant set-up and maintenance. Furthermore, care must be taken when optionally removing the shrunken heat shrink yarn to avoid a combustion process which causes localized areas of high temperature and degradation of the fiberglass yarns.

Copending U.S. patent application: "Vibration Compacted Fabrics For Orthopedic Casting Tapes"—Ser. No. 08/142,177, filed on even date herewith by the assignee of the present invention, discloses an article comprising a fabric sheet (e.g., fiberglass) which has been compacted using an elastomeric yarn and a vibration process. The incorporation of the additional elastomeric yarn(s) into the knit structure requires an additional bar on the knitter and the attendant set-up and maintenance. Furthermore, care must be taken when removing the elastomeric yarn to avoid a combustion process which causes localized areas of high temperature and degradation of the fiberglass yarns.

From the foregoing, it will be appreciated that what is needed in the art is an orthopedic casting material which has both the advantages of plaster of Paris, e.g., good moldability and palpability of the fine bone structure, and the advantages of non-plaster of Paris materials, e.g., good strength-to-weight ratio and good air permeability. In this regard it would be a significant advancement in the art to provide such a combination of advantages without actually using plaster of Paris, thereby avoiding the inherent disadvantages of plaster of Paris outlined herein. It would be a further advancement in the art to provide such non-plaster of Paris orthopedic casting materials which have as good or better properties than the non-plaster of Paris orthopedic casting materials of the prior art. Such orthopedic casting materials and methods for preparing the same are disclosed and claimed herein.

RELATED APPLICATIONS

Of related interest are the following U.S. patent applications, filed on Jan. 25, 1993 by the assignee of this invention: "Mechanically Compacted Fabrics for Orthopedic Casting Tapes"—Ser. No. 08/008,161; and "Microcreping of Fabrics for Orthopedic Casting Tapes"—Ser. No. 08/008,751; and copending U.S. patent applications filed on even date herewith by the assignee of this invention: "Compacted Fabrics for Orthopedic Casting Tapes"—Ser. No. 08/141,830; and "Vibration Compacted Fabrics For Orthopedic Casting Tapes'-'—Ser. No. 08/142,177, which are herein incorporated by reference.

SUMMARY OF THE INVENTION

The present invention provides an article comprising a compacted fiberglass (or other high modulus fiber) fabric sheet and a curable or hardenable resin coated onto the fabric sheet. The fabric sheet is compacted using a lubricating solution thereby providing extensibility to the fabric and then is optionally heat set. The article may be in the form of an orthopedic bandage. The present invention also provides an article comprising a compacted fiberglass fabric sheet and a curable or hardenable resin coated onto the fabric sheet.

DETAILED DESCRIPTION OF THE INVENTION

Figure 1:
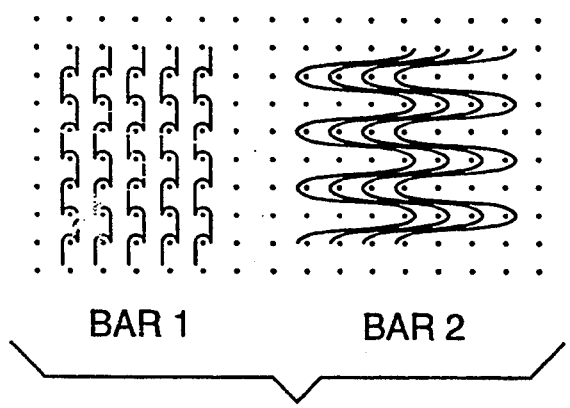
FIG. 1 is a two bar Raschel knit in which bar one performs a simple chain stitch and bar two performs lapping motions to lay in yarn.

The present invention relates to orthopedic casting materials and methods for preparing and using such orthopedic casting materials, wherein the materials comprise a fiberglass backing or fabric which is impregnated with a curable or hardenable liquid resin. In particular, the fabrics employed in the present invention have important characteristics and physical properties which allow the fabrics to be made highly extensible.

One element of this invention is a flexible sheet upon which a curable or hardenable resin can be coated to reinforce the sheet when the resin is cured or hardened thereon. The sheet is preferably porous such that the sheet is at least partially impregnated with the resin. Examples of suitable sheets are knit fabrics comprised of inorganic fibers or materials such as fiberglass. The sheet may alternatively be referred to as the "scrim" or the "backing."

The present invention involves compacting a fabric sheet using a lubricating solution to assist in imparting stretchability and conformability to the fabric while minimizing undesirable recovery forces.

Suitable fabrics, after compaction, have important characteristics and physical properties which allow the fabrics to be loaded with resin to the extent needed to provide proper strength as an orthopedic casting material, while providing necessary porosity as well as improved extensibility leading to improved conformability, tactile manipulability, moldability, and palpability. Several important criteria for choosing a fabric which will provide the characteristics necessary for purposes of the present invention include: (1) lengthwise extensibility and conformability after compaction, and the related characteristics of moldability, tactility, and palpability once the fabric has been resin impregnated; (2) resin loading capacity; and (3) porosity. It is important that each of these parameters be carefully controlled in providing fabrics which will successfully form orthopedic casting materials (e.g., casts having high strength and good layer-to-layer lamination strength) within the scope of the present invention.

Extensibility is important from the standpoint that the fabric must be extensible enough along its length, i.e., in the elongated direction, so that the resultant orthopedic casting material can be made to substantially conform to the body part to which it is applied. Materials which are not sufficiently extensible in the elongated direction do not conform well to the body part when wrapped therearound, often resulting in undesirable wrinkles or folds in the material. On the other hand, the extensibility of the fabric in the elongated direction should not be so high that the material is too stretchy, resulting in a material structure which may be deformed to the extent that strength is substantially reduced.

For purposes of the present invention, the coated fabric, after compaction and after being coated with a curable liquid resin, should have from about 10% to about 200% extensibility in the elongated direction when a 2.63N tensile load or force is applied per 1 cm wide section of the fabric, and preferably from about 25% to about 100% extensibility in the elongated direction when a 2.63N tensile load or force is applied per 1 cm wide section of the fabric, and more preferably from about 35% to about 65% extensibility in the elongated direction when a 2.63N tensile load or force is applied per 1 cm wide section of the fabric.

Although not nearly as critical, it is also desirable that the fabric employed have some extensibility along its width, i.e., in the direction transverse to the elongated direction. Thus although the fabric may have from 0% to 100% extensibility in the transverse direction, it is presently preferable to use a fabric having from about 1% to about 30% extensibility in the transverse direction when a 2.63N tensile load or force is applied per 1 cm wide section of the fabric.

The fabrics of the present invention, after compaction, although stretchable, are preferably not overly elastic or resilient. Fabrics which are overly elastic, when used as backings for orthopedic bandages, tend to cause undesirable constriction forces around the wrapped limb or body part. Thus, once the resin impregnated fabric has been stretched and applied around a body part, the stretched material preferably maintains its shape and does not revert back to its unstretched position.

The resin loading capacity or ability of the fabric to hold resin is important from the standpoint of providing an orthopedic casting material which has sufficient strength to efficaciously immobilize a body part. The surface structure of the fabric, including the fibers, interstices, and apertures, is very important in providing proper resin loading for purposes of the present invention. In this regard, the interstices between the fibers of each fiber bundle must provide sufficient volume or space to hold an adequate amount of resin within the fiber bundle to provide the strength necessary; while at the same time, the apertures between fiber bundles preferably remain sufficiently unoccluded such that adequate porosity is preserved once the cast is applied. Thus, the interstices between fibers are important in providing the necessary resin loading capacity, while the apertures are important in providing the necessary porosity for the finished cast. However, a balancing of various parameters is needed to achieve both proper resin loading and porosity. The coated fabric should have preferably between about 6 and 70 openings (i.e., apertures) per square cm, more preferably between about 10 and 50 openings per square cm, and most preferably between about 20 and 40 openings per square cm when measured under a tensile load of 2.63N/cm width. As used herein an "opening" is defined as the area defined by adjacent wales and in-lay members. The number of openings per unit area is therefore determined by multiplying the number of wales by the number of courses and dividing by the area.

As used herein, a "compacted" fiberglass sheet is one in which extensibility is imparted to the fabric due to the structural relaxation of loops by the "wet compaction" processes described herein. The wet compaction process is presently believed to impart extensibility to the fabric by "stress relaxing" the loops of the knit as described herein. Typically, when a fabric is knitted the inside surfaces of two adjacent rows of loops are in contact or nearly in contact and the loops are distorted in the lengthwise direction (e.g., in the shape of an oval). This contact and/or distortion is the result of the fabric being under tension while the knit is being formed. Each successive row of loops (i.e., chain stitches) is, in effect, formed against the preceding row of loops. The wet compaction process of the present invention imparts fabric compaction by relaxing the loops (i.e., to a lower stress configuration) and optionally setting or annealing the fabric in the compacted form. Extensibility is thus imparted to the fabric due to the greater capacity of the more circular loops to be deformed. When tension is again applied to the fabric the loops can return to their original "stressed" position, i.e., the position they occupied when originally knit.

Fiberglass knitted fabrics with good extensibility are achievable with two common knitting methods: Raschel and tricot. Raschel knitting is described in "Raschel Lace Production" by B. Wheatley (published by the National Knitted Outerwear Association, 51 Madison Avenue, New York, N.Y. 10010) and "Warp Knitting Production" by Dr. S. Raz (published by Heidelberger Verlagsanstadt und Druckerei GmbH, Hauptstr. 23, D-6900 Heidelberg, Germany). Two, three and four bar Raschel knits can be produced by regulating the amount of yarn in each stitch. Orthopedic casting tape fabrics are generally two bar Raschel knits although extra bars may be employed. Factors which affect the extensibility of fiberglass Raschel knits are the size of the loops in the "chain" stitch, especially in relation to the diameter(s) of the yarn(s) which passes through them, and the amount of a loose yarn in the "lay-in" or "laid-in" stitch(es). If a chain loop is formed and two strands of lay-in yarn pass through it which nearly fill the loop, then the loop resists deformation and little stretch will be observed. Conversely, if the lay-in yarns do not fill the loop, then application of tension will deform the loop to the limits of the lay-in yarn diameter and stretch will be observed.

Typical bar patterns for the knit fabric substrates of the present invention are shown in the drawings.

FIG. 1 is a two bar Raschel knit in which bar one performs a simple chain stitch and bar two performs lapping motions to lay in yarn.

Figure 2:
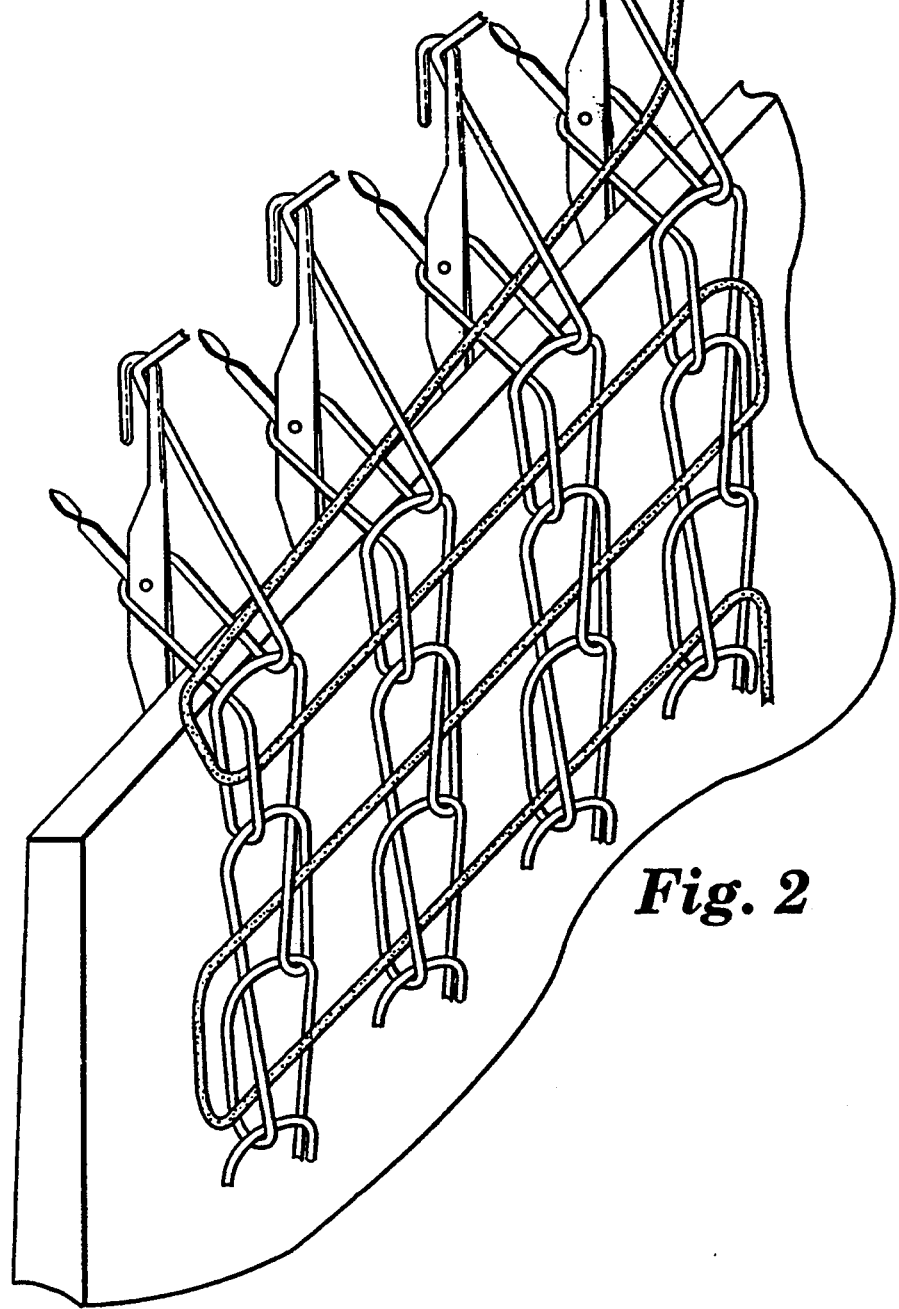
FIG. 2 is a depiction of a two bar Raschel knit in which bar one performs a simple chain stitch and bar two performs lapping motion to lay in yarn. The bars are depicted in a overlapping view.

FIG. 2 is a depiction of a two bar Raschel knit in which bar one performs a simple chain stitch and bar two performs lapping motion to lay in yarn. The bars are depicted in a overlapping view.

It should be understood that the above bar patterns may be modified. For example, FIG. 2 may be modified by increasing or decreasing the number of chain stitches crossed by a particular lay-in stitch. Furthermore, additional lay-in stitches may be employed using, for example, a third bar.

For orthopedic casting material, the fabric selected (preferably fiberglass), in addition to having the extensibility requirement noted above, should be of a suitable thickness and mesh size to insure good penetration of the curing agent (e.g., water) into the roll of resin-coated tape and to provide a finished cast with adequate strength and porosity. Such fabric parameters are well-known to those skilled in the art and are described in U.S. Pat. No. 4,502,479 which is herein incorporated by reference.

The present invention is to a method of compacting high modulus knits by the "wet compaction" processes described herein to achieve a highly extensible high strength fabric. It is presently believed that this process will work for a variety of high modulus materials including fiberglass, ceramic fibers such as Nextel ™, and polyaramides fibers such as Kevlar. While not being bound to any theory, the process is believed to result in fabric compaction due to the high modulus yarns relaxing to a lower stress configuration in the presence of a lubricating solution. For example, after being knit fiberglass fabrics typically have "oval" shaped loops in the wale stitch resulting from the tension applied by the take up rollers when removing the fabric from the needle bed. A loop having a "circular"

shape, i.e., having a larger minimum radius of curvature, would have a lower energy than a more stressed oval loop. Attaining this lower stress configuration results in compaction of the fabric.

The "wet compaction" process comprises the steps of: knitting a high modulus yarn to form a fabric comprising adjacent rows of loops; contacting the knit fabric with a lubricant (preferably a lubricating solution); allowing or assisting the loops to stress relax; and optionally removing (e.g., by drying) the lubricant from the knit. The lubricant may preferably comprise a lubricating solution (e.g., water) and may be rinsed from the knit, if desired, after the knit has been relaxed. The relaxed knit may optionally be heat set to prevent or decrease fraying.

In order to achieve effective compaction of the knit it is necessary to contact the knit fabric with effective amounts of a lubricant. Commercial fiberglass yarns are often sized with a lubricating composition in order to facilitate processing (such as warping and knitting) and to prevent damage to the yarn during such processing. For example, some typical commercial sizings comprise starch and oil mixtures and may include additional additives and processing aides. In the case of ECDE 75 1/0 0.7Z fiberglass from PPG Industries the sizing is believed to be present at a level of approximately 1% by weight (0.75–1.35%). While this type and amount of sizing apparently facilitates production of the knit, it does not sufficiently lubricate the fabric so as to "wet compact" the fabric to a high stretch configuration.

Ideally, a sufficient level of lubrication is imparted to the fabric in the sizing alone to facilitate compaction. Alternatively, it is sufficient and desirable to additionally lubricate the knit with a suitable lubricating fluid. Preferably the fabric is immersed in the lubricant but other techniques such as spraying the fabric with a lubricant or passing the fabric through a lubricating vapor are desirable.

Suitable lubricants include any substance that controls or reduces the coefficient of friction between two surfaces (e.g., two contacting glass fiber surfaces). Suitable lubricants come in a wide variety of forms and modes of application. For example, neat liquids, solvent solutions, and solids such as powders and flakes may be employed. The lubricant may be applied to the surface of the fabric by any of the standard coating methods, including brushing, dipping, dusting, spraying, electrostatic coating, etc.

Suitable liquid lubricants include water, organic solvents, silicone fluids, and fluorinated compounds. Suitable organic solvents include alcohols such as methanol, ethanol, 1-propanol, 2-propanol, and 2-methyl-2-propanol, ketones such as acetone and methyl ethyl ketone, aldehydes such as formaldehyde, acetaldehyde, propionaldehyde, acrolein, glutaraldehyde and 2-hydroxyadipaldehyde, amides such as acetamide esters such as ethylacetate and propylacetate, diesters such as diesters of succinic and glutaric acid, ethers such as tetrahydrofuran, propyleneglycols, ethyleneglycols, monoalkyl and dialkyl esters of glycols, and other substances such as n-methylpyrolidone and dimethyl sulfoxide. Of the suitable lubricants, water is presently preferred as this is most convenient and safe. Water is also believed to solubilize the starch sizing thereby increasing the lubricity of the sizing. Furthermore, a water lubricant does not contribute to an exothermic combustion reaction during subsequent heat setting of the fabric. A water lubricant may actually remove some of the commercially applied "sizing" and thereby reduce potential exothermic combustion reactions caused by the sizing.

Preferably, when the lubricant is water, the water is applied to the fabric at an elevated temperature, e.g., 60°–90° C. More preferably, when the lubricant is water based, the water contains a detergent or surfactant which not only helps lubricate the fabric but also assists in the removal of any sizing. Once the sizing is effectively removed the fabric is "locked" into its compacted configuration in the sense that a significantly higher tensile force is required to extend the fabric and is therefore much more easy to collect by subsequent operations such as winding onto a core into a roll. When selecting a detergent or lubricating solution it is important to ensure that any materials left on the fabric (or on individual fibers) by the cleaning process are compatible with the curable resin. For example, if the fabric is to be coated with an isocyanate functional prepolymer resin, preferred lubricants would not contain organic or inorganic strongly basic impurities which could result in side reactions such as trimerization and allophonate formation. These side reactions can result in an increase in resin viscosity and thereby make the product eventually unusable. While organic basic impurities are easily removed in a subsequent heat setting process, inorganic bases may still remain and should therefore be particularly avoided. Similarly, strongly acidic impurities should be avoided due to potential inactivation of tertiary amine catalysts which may be present in the resin formulation. Therefore, preferred lubricants are substantially free of acidic or basic impurities which can limit the shelf life or alter the cure properties of the resin.

After lubricating the fabric with a suitable lubricant as previously described, the fabric loops are allowed to stress relax. One method to assist this relaxation is to vibrate the lubricated fabric. For example, simply shaking the lubricated fabric composition is sufficient to effect compaction, however, such a process does not lend itself well to commercial scale application. Preferably, the knitted fabric is passed directly into a lubricating/washing bath. While in the lubricating bath the fabric may be vibrated by any suitable method including: sonic and ultrasonic vibration, mechanical vibration, agitation of the bath, and the like. The fabric is vibrated until the desired degree of compaction has been achieved. It should be noted that the amount of extensibility imparted to any particular fabric will be a function of the fabric construction. Therefore, knitting parameters such as runner length, knit pattern, and stitch length are important parameters which will determine the maximum amount of extensibility imparted to a fabric.

As outlined above, it may be desirable to rinse the fabric after compacting. This is desired not only to remove residual impurities which could result in poor resin aging but also to remove the lubricant and thereby effectively "lock" the knit into the compacted state. Surprisingly, it has been found that once a majority of the sizing is removed (e.g., in a scouring step with either hot water or a hot detergent solution) the compacted fabric resists being pulled back out. This enables the dried fabric to be easily handled by automatic equipment (such as winding equipment) without losing its compacted form. "Locking" the fabric into a compacted state facilitates collecting the fabric and coating the fabric since both of these operations must be done with some degree of tension on the fabric. Ideally the fabric is passed continuously through multiple rinse stations and then dried. Rinsing may be accomplished by passing the fabric through a bath or by spraying the fabric while it is supported on a porous belt. Drying may be accomplished using convection heating, IR lamps, heated roller, microwave, etc. Notably, coating the compacted fabric with a liquid resin may cause the "lock" to be lost or reduced. Therefore, care should be taken to not apply tension to such coated compacted fabrics that would distort the fabric and reduce its subsequent extensibility.

In processing the knitted fiberglass fabric of the present invention, a length of fabric is optionally, and preferably, heat-set while the fabric is in a compacted form. Preferably, the fabric is compacted and then wound onto a cylindrical core so large batches can be heat set at one time in a single oven. Care must be taken to avoid applying undue tension to the fabric (before the heat set has occurred) which would distort the knots and loops and pull out the extensibility imparted by the compacting process. Alternatively, the fabric may be stabilized in order to resist low tension handling forces. Since the fabric must be collected in some manner as it comes off the knitter, e.g., wound, a certain amount of tension may be required. In a preferred method of the present invention, a significant amount of tension can be applied to the fabric once the fabric has been washed free of most or all of its sizing. Removal of the sizing and drying the fabric in its compacted form produces a fabric which is resistant to extension. This is illustrated in Example 2.

A continuous heat-setting process may also be used in which a length of fabric is first compacted by the wet compaction process described herein and then the compacted fabric is placed on a moving conveyor system and passed through an oven for a sufficient time and temperature to achieve heat setting of the fabric. Alternatively, one may use the same oven to both "lock" the compacted fabric (e.g., by drying the lubricant) and heat set the fiberglass yarns.

The heat-setting step may be performed in a number of conventional ways known to the art. In heat-setting a small piece of fiberglass fabric, e.g., 25 centimeters of tape, in a single layer, a temperature of 425° C. for three minutes has been found to be sufficient. Equivalent setting at lower temperatures is possible, but longer time is required. In general, batch processes require a longer residence time at the selected temperature due to the mass of glass fabric which must be heated and the need to remove all traces of sizing material which may undesirably color the final fabric.

The optimum heat-setting process described above is sufficient in most cases to remove any sizing not previously removed by rinsing and drying the lubricant from the fabric. In general, to completely desize the fiberglass tape and not leave any visible residue it is necessary to heat the tape to a temperature between 370° and 430° C., more preferably between 400° and 430° C. The closer you get to 430° C. the shorter the cycle and more efficient the operation. Although the tape could be cleaned at higher temperatures, this may cause permanent degradation of the fiberglass fabric. For example, when the temperature of the fabric exceeds 480° C. and especially when the temperature exceeds 540° C. the tensile strength of the knit decreases very rapidly. When the tape is exposed to temperatures over 590° C. it becomes very brittle and wrapping a cast using normal tension is precluded. A preferred heat desizing cycle raises the oven temperature to about 430° C. and maintains that temperature until the tape is clean (e.g., about 6-8 hours in a recirculating oven). However, obtaining this result is somewhat complicated since the tape's temperature is affected by both the heat of the oven and the heat of combustion resulting from burning the sizing.

Controlling the exotherm from organic material in the knit is essential and can be accomplished most easily and economically by limiting the total amount of added organic material (e.g., sizing) which must be removed. In order to knit a fiberglass yarn without excessive damage a sizing is preferably present. Preferably the amount of sizing utilized is the minimum level necessary to prevent damage during knitting. A preferred amount of sizing for fiberglass fabrics is between 0.75 and 1.35% (based on weight of the fabric).

Finally, it has been observed that the jumbo's winding tension can greatly influence the exothermic temperature rise due to combustion and therefore adversely affect web integrity. In general, jumbos wound under higher tension tend to reach a lower peak temperature and have a greater web integrity than those wound more loosely. It is believed that the organic content of more tightly wound jumbos burn more slowly and therefore have lower peak internal temperatures. While not intending to be bound by theory, this result is believed to be due to oxygen starvation within the jumbo. Within a jumbo (i.e., away from the surface of the roll) the availability of oxygen is controlled by the diffusion rate into the jumbo. Careful control of the roll's permeability to oxygen can be utilized to control the rate of combustion of the organic material.

Alternatively, one may "set" the ends of the compacted fabrics of the present invention through the use of very soft conformable binders as described in U.S. Pat. No. 4,800,872 which is herein incorporated by reference.

If desired, reactive functional silanes, titanates and/or zirconates could be added to the sizing. It is believed that such silanes would not be easily washed off since they would be covalently bound to the fiber surface. Alternatively, the silanes could be added to the fiber surface at the wet compacting step, e.g., in the lubricating tank.

The fabric is preferably cooled prior to application of the resin. The resin is preferably coated on the fabric using an operation that minimizes the tension applied to the fabric. The tension applied after the resin is applied is critical since the resin will generally lubricate the fabric and allow it to extend much more easily. Therefore, a low tension coating process should be employed.

In one embodiment of the present invention, a fiberglass fabric is knit according to the process described herein, compacted by the wet compaction process described herein, and then heat set in the compacted form. The compacted fabric is then coated with a curable resin. There are many advantages to this process over conventional knitting processes. First, unlike traditional uncompacted knit fiberglass fabrics, the fabric produced by this method has increased extensionability. Second, there is no need to knit a heat shrink yarn or an elastic yarn into the fabric to increase extensibility. Unlike these compaction methods, the present invention does not, in general, add combustible material to the fabric and in the preferred mode removes a substantial portion of the combustible sizing prior to heat setting. Therefore, the compacted fabrics of the present invention have very good integrity—as good or better than conventional heat set fiberglass fabrics.

Suitable fabrics, after compaction, are compacted to between about 30 and 90 percent of their original dimension. More preferably, the fabric is compacted to between about 50 and 80 percent of its original dimension. Most preferably, the fabric is compacted to between about 60 and 75 percent of its original dimension.

The resin selected to apply to the heat-set fabric is dictated by the end-use of the product. For orthopedic casting materials, suitable resins are well-known and described for example, in U.S. Pat. Nos. 4,376,438; 4,433,680; 4,502,479; and 4,667,661 and U.S. patent application Ser. No. 07/376,421 which are herein incorporated by reference. The presently most preferred resins are the moisture-curable isocyanate-terminated polyurethane prepolymers described in the aforementioned patents. Alternatively, one may employ one of the resin systems described herein. The amount of such resin applied to the fiberglass tape to form an orthopedic casting material is typically an amount sufficient to constitute 35 to 50 percent by weight of the final "coated" tape. The term "coated" or "coating" as used herein with respect to the resin refers generically to all conventional processes for applying resins to fabrics and is not intended to be limiting.

To insure storage stability of the coated tape, it must be properly packaged, as is well known in the art. In the case of water-curable isocyanate-terminated polyurethane prepolymer resin systems, moisture must be excluded. This is typically accomplished by sealing the tape in a foil or other moisture-proof pouch.

The curable or hardenable resins useful in this invention are resins which can be used to coat a sheet material and which can then be cured or hardened to reinforce the sheet material. For example, the resin is curable to a crosslinked thermoset state. The preferred curable or hardenable resins are fluids, i.e., compositions having viscosities between about 5 Pa s and about 500 Pa s, preferably about 10 Pa s to about 100 Pa s.

The resin used in the casting material of the invention is preferably any curable or hardenable resin which will satisfy the functional requirements of an orthopedic east. Obviously, the resin must be nontoxic in the sense that it does not give off significant amounts of toxic vapors during curing which may be harmful to either the patient or the person applying the east and also that it does not cause skin irritation either by chemical irritation or the generation of excessive heat during cure. Furthermore, the resin must be sufficiently reactive with the curing agent to insure rapid hardening of the cast once it is applied but not so reactive that it does not allow sufficient working time to apply and shape the cast. Initially, the casting material must be pliable and formable and should adhere to itself. Then in a short time following completion of cast application, it should become rigid or, at least, semi-rigid, and strong to support loads and stresses to which the east is subjected by the activities of the wearer. Thus, the material must undergo a change of state from a fluid-like condition to a solid condition in a matter of minutes.

The preferred resins are those cured with water. Presently preferred are urethane resins cured by the reaction of a polyisocyanate and a polyol such as those disclosed in U.S. Pat. No. 4,131,114. A number of classes of water-curable resins known in the an are suitable, including polyurethanes, cyanoacrylate esters, epoxy resins (when combined with moisture sensitive catalysts), and prepolymers terminated at their ends with trialkoxy- or trihalosilane groups. For example, U.S. Pat. No. 3,932,526 discloses that 1,1-bis(perfluoromethylsulfonyl)-2-aryl ethylenes cause epoxy resins containing traces of moisture to become polymerized.

Resin systems other that those which are water-curable may be used, although the use of water to activate the hardening of an orthopedic casting tape is most convenient, safe and familiar to orthopedic surgeons and medical casting personnel. Resin systems such as that disclosed in U.S. Pat. No. 3,908,644 in which a bandage is impregnated with difunctional acrylates or methacrylates, such as the bis-methacrylate ester derived from the condensation of glycidyl methacrylate and hisphenol A (4,4'-isopropylidenediphenol) are suitable. The resin is hardened upon wetting with solutions of a tertiary amine and an organic peroxide. Also, the water may contain a catalyst. For example, U.S. Pat. No. 3,630,194 proposes an orthopedic tape impregnated with acrylamide monomers whose polymerization is initiated by dipping the bandage in an aqueous solution of oxidizing and reducing agents (known in the art as a redox initiator system). The strength, rigidity and rate of hardening of such a bandage is subjected to the factors disclosed herein. Alternatively, hardenable polymer dispersions such as the aqueous polymer dispersion disclosed in U.S. Pat. No. 5,169,698, which is herein incorporated by reference, may be used in the present invention.

Some presently more preferred resins for use in the present invention are water-curable, isocyanate-functional prepolymers. Suitable systems of this type are disclosed, for example, in U.S. Pat. No. 4,411,262, and in U.S. Pat. No. 4,502,479. Preferred resin systems are disclosed in U.S. Pat. No. 4,667,661 and U.S. patent application Ser. No. 07/376,421. The following disclosure relates primarily to the preferred embodiment of the invention wherein water-curable isocyanate-functional prepolymers are employed as the curable resin. A water-curable isocyanate-functional prepolymer as used herein means a prepolymer derived from polyisocyanate, preferably aromatic, and a reactive hydrogen compound or oligomer. The prepolymer has sufficient isocyanate-functionality to cure (i.e., to set or change from a liquid state to a solid state) upon exposure to water, e.g., moisture vapor, or preferably liquid water.

It is preferred to coat the resin onto the fabric as a polyisocyanate prepolymer formed by the reaction of an isocyanate and a polyol. Suitable isocyanates include 2,4-toluene diisocyanate, 2,6-toluene diisocyanate, mixture of these isomers, 4,4'-diphenylmethane diisocyanate, 2,4'-diphenylmethane diisocyanate, mixture of these isomers together with possible small quantities of 2,2'-diphenylmethane diisocyanate (typical of commercially available diphenylmethane diisocyanate), and aromatic polyisocyanates and their mixtures such as are derived from phosgenation of the condensation product of aniline and formaldehyde. It is preferred to use an isocyanate which has low volatility such as diphenylmethane diisocyanate (MDI) rather than a more volatile material such as toluene diisocyanate (TDI). Typical polyols for use in the prepolymer system include polypropylene ether glycols (available from Arco Chemical Co. under the trade name Arcol ™ PPG and from BASF Wyandotte under the trade name Pluracol ™), polytetramethylene ether glycols (Polymeg ™ from the Quaker Oats Co.), polycaprolactone diols (Niax TM PCP series of polyols from Union Carbide), and polyester polyols (hydroxyl terminated polyesters obtained from esterification of dicarboxylic acids and diols such as the Rucoflex TM polyols available from Ruco division, Hooker Chemical Co.). By using high molecular weight polyols, the rigidity of the cured resin can be reduced.

An example of a resin useful in the casting material of the invention uses an isocyanate known as Isonate TM 2143L available from the Upjohn Company (a mixture containing about 73% of MDI) and a polypropylene oxide polyol from Arco known as Arcol TM PPG725. To prolong the shelf life of the material, it is preferred to include from 0.01 to 1.0 percent by weight of benzoyl chloride or another suitable stabilizer.

The reactivity of the resin once it is exposed to the water curing agent can be controlled by the use of a proper catalyst. The reactivity must not be so great that: (1) a hard film quickly forms on the resin surface preventing further penetration of the water into the bulk of the resin; or (2) the cast becomes rigid before the application and shaping is complete. Good results have been achieved using 4-[2-[1-methyl-2-(4-morpholinyl)ethoxy]ethyl]morpholine (MEMPE) prepared as described in U.S. Pat. No. 4,705,840, the disclosure of which is incorporated by reference, at a concentration of about 0.05 to about 5 percent by weight.

Foaming of the resin should be minimized since it reduces the porosity of the cast and its overall strength. Foaming occurs because carbon dioxide is released when water reacts with isocyanate groups. One way to minimize foaming is to reduce the concentration of isocyanate groups in the prepolymer. However, to have reactivity, workability, and ultimate strength, an adequate concentration of isocyanate groups is necessary. Although foaming is less at low resin contents, adequate resin content is required for desirable cast characteristics such as strength and resistance to peeling. One satisfactory method of minimizing foaming is to add a foam suppressor such as silicone Antifoam A (Dow Corning), or Antifoam 1400 silicone fluid (Dow Corning) to the resin. It is especially preferred to use a silicone liquid such as Dow Corning Antifoam 1400 at a concentration of about 0.05 to 1.0 percent by weight. Water-curable resins containing a stable dispersion of hydrophobic polymeric particles, such as disclosed in U.S. patent application Ser. No. 07/376,421 and laid open as European Published Patent Application EPO 0 407 056, may also be used to reduce foaming.

Also included as presently more preferred resins in the present invention are non-isocyanate resins such as water reactive liquid organometallic compounds. These resins are especially preferred as an alternative to isocyanate resin systems. Water-curable resin compositions suitable for use in an orthopedic cast consist of a water-reactive liquid organometallic compound and an organic polymer. The organometallic compound is a compound of the formula $(R^1O)_xMR^2_{y-x}$ wherein: each $R^1$ is independently a $C_1-C_{100}$ hydrocarbon group, optionally interrupted in the backbone by 1–50 nonperoxide —O—, —S—, —C(O)—, or

groups; each $R^2$ is independently selected from the group consisting of hydrogen and a $C_1-C_{100}$ hydrocarbon group, optionally interrupted in the backbone by 1–50 nonperoxide —O—, —S—, —C(O)—, or

groups; x is an integer between 1 and y, inclusive; y is the valence of M; and M is boron, aluminum, silicon, or titanium. The organic polymer is either an addition polymer or a condensation polymer. Addition polymers are preferably utilized as the organic polymer constituent. Particularly useful addition polymers are those made from ethylenically unsaturated monomers. Commercially available monomers, from which such addition polymers can be formed, include but are not limited to, ethylene, isobutylene, 1-hexene, chlorotrifluoroethylene, vinylidene chloride, butadiene, isoprene, styrene, vinyl napthalene, ethyl acrylate, 2-ethylhexyl acrylate, tetrahydrofurfuryl acrylate, benzyl acrylate, poly(ethylene oxide) monoacrylate, heptafluorobutyl acrylate, acrylic acid, methyl methacrylate, 2-dimethylaminoctyl methacrylate, 3-methacryloxypropyltris(trimethylsiloxy)silane, isobutyl methacrylate, itaconic acid, vinyl acetate, vinyl stearate, N,N-dimethylacrylamide, tert-butyl acrylamide, acrylonitrile, isobutyl vinyl ether, N-vinyl pyrrolidinone, vinyl azlactone, glycidyl methacrylate, 2-isocyanatoethyl methacrylate, maleic anhydride, vinyl triethoxysilane, vinyl tris(2-methoxyethoxy)silane, and 3-(trimethoxysilyl)propyl methacrylate. Polymers bearing hydrolyzable functionality are preferred. An acidic or basic catalyst may be used to accelerate the water cure of these compositions. Strong acid catalysts are preferred.

Also included as presently more preferred resins in the instant invention are alkoxysilane terminated resins, i.e., prepolymers or oligomers, having a number average molecular weight of about 400–10,000, preferably about 500–3,000. A polymer forms upon contacting the alkoxysilane terminated prepolymer with water as a result of condensation of molecules of this prepolymer with other molecules of the same prepolymer. Each molecule of the prepolymer or oligomer contains at least one hydrolyzable terminal alkoxysilane group. Compounds of Formula I useful in the resin compositions of the present invention may contain one to six terminal alkoxysilane groups per 5 molecule. Preferably, the alkoxysilane terminated resin is a urethane-based resin, i.e., a prepolymer containing —NH—C-(O)—O—group(s), or a urea resin, i.e., a prepolymer containing

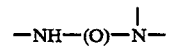

group(s), or a resin containing both urea and urethane groups. More preferably, the resin is urea/urethane-based.

The water-reactive alkoxysilane terminated resin having at least one hydrolyzable terminal alkoxysilane group per molecule is preferably a compound of the formula (Formula I):

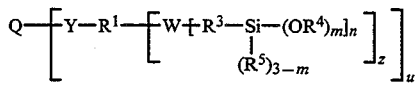

wherein:
Q is a polyol residue;
W is —NH—C(O)—X(R²₂₋ₙ₋q)— or —X—C(O)—NH—;
X is

—O—, or —S—;
Y is

—O—, —S—, carbamylthio (—S—C(O)—NH—), carbamate (—O—C(O)—NH—), or substituted or N-substituted ureido (—N(C(O)—NH—) —);

R¹ is a substituted or unsubstituted divalent bridging C₁-C₁₀₀ hydrocarbon group, optionally interrupted in the backbone by 1-50 nonperoxide —O—, —C(O)—, —S—, —SO₂—, —NR⁶—, amide (—C(O)—NH—), ureido (—NH—C(O)—NH—), carbamate (—O—C(O)—NH—), carbamylthio (—S—C(O)—NH—), unsubstituted or N-substituted allophonate (—NH—C(O)—N(C(O)—O—)—), unsubstituted or N-substituted biuret (—NH—C(O)—N(C(O)—NH)—), and N-substituted isocyanurate groups;

R² can be present or absent, and is selected from the group consisting of H and a substituted or unsubstituted C₁-C₂₀ hydrocarbon group, optionally interrupted in the backbone by 1-10 nonperoxide —O—, —C(O)—, —S—, —SO₂—, or —NR⁶— groups;

R³ is a substituted or unsubstituted divalent bridging C₁-C₂₀ hydrocarbon group, optionally interrupted in the backbone by 1-5 nonperoxide —O—, —C(O)—, —S—, —SO₂—, or —NR⁶— groups;

R⁴ is a C₁-C₆ hydrocarbon group or —N=C(R⁷)₂;
each R⁵ and R⁷ is independently a C₁-C₆ hydrocarbon group;
R⁶ is a H or a C₁-C₆ hydrocarbon group;
n=1-2 and q=0-1, with the proviso that when X is N, n+q=1, and when X is S or O, n+q=2;
u=the functionality of the polyol residue=0-6, with the proviso that when u=0, the compound of Formula I is

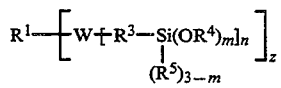

m=2-3; and
z=1-3.

It is to be understood that each "R³—Si(R⁵)₃₋ₘ(OR⁴)ₘ" moiety can be the same or different. When used in Formula I, the Y and R¹ groups that are not symmetric, e.g., amide (—C(O)—NH—) and carbamylthio (—S—C(O)—NH—) groups, are not limited to being bound to adjacent groups in the manner in which these groups are represented herein. That is, for example, if R¹ is carbamate (represented as —O—C(O)—NH—), it can be bound to Y and W in either of two manners: —Y—O—C(O)—NH—W— and —W—O—C(O)—NH—Y—.

Herein, when it is said that "each" R⁵ and R⁷ is "independently" some substituent group, it is meant that generally there is no requirement that all R⁵ groups be the same, nor is there a requirement that all R⁷ groups be the same. As used herein, "substituted" means that one or more hydrogen atoms are replaced by a functional group that is nonreactive, e.g., to hydrolysis and/or condensation and noninterfering with the formation of the cured polymer.

In preferred materials R¹ is selected from the group consisting of a substituted or unsubstituted C₁-C₂₀₀ alkyl, a substituted or unsubstituted C₁-C₂₀₀ acyl, and groups of up to 50 multiples of a C₃-C₁₈ cycloalkyl, a C₇-C₂₀ aralkyl, and a C₆-C₁₈ aryl. By this, it is meant that R¹ can be a long chain containing, for example, up to 50 repeating C₆-C₁₈ aryl groups. More preferably, R¹ is selected from the group consisting of a substituted or unsubstituted C₁-C₁₀₀ alkyl, a substituted or unsubstituted C₁-C₁₀₀ acyl, and groups of up to 30 multiples of a C₅-C₈ cycloalkyl, and a C₆-C₁₀ aryl. Most preferably, R¹ is selected from the group consisting of a C₁-C₂₀ alkyl, a C₁-C₈ acyl, and groups of up to 5 multiples of a C₅-C₈ cycloalkyl, and a C₆-C₁₀ aryl. In each of the preferred R¹ groups, the backbone is optionally interrupted by 1-20 nonperoxide —O—, —C(O)—, —S—, —SO₂—, —NR⁶—, amide, ureido, carbamate, carbamylthio, allophonate, biuret, and isocyanurate groups.

In each of the more preferred R¹ groups, the backbone is optionally interrupted by 1-10 nonperoxide —O—, —C(O)—, —S—, —SO₂—, —NR⁶—, amide, ureido, carbamate, carbamylthio, allophonate, biuret, and isocyanurate groups. In each of the most preferred R¹ groups, the backbone of each of the R¹ groups is not interrupted by any of these groups.

In preferred materials, each of R² and R³ is independently selected from the group consisting of a substituted or unsubstituted C₁-C₂₀ alkyl, a substituted or unsubstituted C₂-C₁₈ alkenyl, and groups of up to 10 multiples of a C₃-C₁₈ cycloalkyl and a C₆-C₁₈ aryl. More preferably, each R² and R³ is independently selected from the group consisting of a substituted or unsubstituted C₁-C₁₀ alkyl, a substituted or unsubstituted C₂-C₁₀ alkenyl, a C₅-C₈ cycloalkyl, and a C₆-C₁₀ aryl. Most preferably, each R² and R³ is independently selected from the group consisting of a C₁-C₆ alkyl, a C₂ alkenyl, a C₅-C₈ cycloalkyl, and a C₆ aryl. In each of the preferred R² and R³ groups, the backbone is optionally interrupted by 1-5 nonperoxide —O—, —C(O)—, —S—, —SO₂—, and —NR⁶— groups. In optimal resins, the backbone of each of the R² and R³ groups is not interrupted by any of these groups.

In preferred materials, each of R⁴, R⁵, R⁶, and R⁷ is independently a C₁-C₆ alkyl group. More preferably, each is a C₁-C₃ alkyl group. A single prepolymer according to Formula I can be used in the resin composition of the present invention. Alternatively, a mixture of several different prepolymers according to Formula I can be used in the resin composition.

Optionally, the scrims of the present invention are coated with a resin which incorporates microfiber fillers. These preferred orthopedic bandages enjoy many benefits, for example, resins which incorporate microfiber fillers exhibit: a dramatic increase in strength when coated on the backings of the present invention; an increased "early strength" upon curing; an improved durability and increased modulus; better layer-to-layer lamination strength; a lower exotherm upon setting; and a lower effective resin cost compared to resins which do not incorporate such microfiber fillers. In addition, resin suspensions employing the microfiber fillers of the present invention exhibit generally very little increase in resin viscosity—thereby ensuring easy unwind of the casting bandage and good handling properties such as drapability. Suitable microfibers for use in the present invention include those microfiber fillers disclosed in U.S. patent application Ser. No. 08/008,755 which is herein incorporated by reference.

In addition to the application of the present invention to the field of orthopedic casting tapes, other uses may include wrapping and/or joining pipes, cables or the like; patching or bridging gaps to provide a surface for filling and repairs; etc.

The following examples are offered to aid in understanding of the present invention and are not to be construed as limiting the scope thereof. Unless otherwise indicated, all parts and percentages are by weight.

EXAMPLE 1

Three samples of fiberglass knit (82.5 mm wide and approximately 61 m long) prepared according to the example of U.S. Pat. No. 4,609,578 (which is herein incorporated by reference) were loosely rolled up on a 76 mm diameter core. The cores were removed and the tape placed in individual 4 liter mason jars containing the following solutions:

TABLE 1A

| Component | Run 1 | Run 2 | Run 3 |
|---|---|---|---|
| Water (60° C.) | 2300 gm | 2200 | 2340 |
| Alconox Detergent[1] | — | 18.8 | — |
| Steol CA-460[2] | — | — | 22.0 |
| Fiberglass | 204 | 200 | 207 |

[1]Available from VWR Scientific, San Francisco, CA
[2]An ionic polyethoxylated surfactant available from Stepan Company, Northfield, IL.

The contents of each jar were heated, without agitation, to 79° C. The jars were then sealed and placed on a mechanical shaker for 15 minutes. The solutions were decanted off and the tape rinsed with 3 volumes of hot (60° C.) water. The tape was untangled and gently rewound by hand onto a 76 mm diameter core. The core was removed and the tape placed in an aluminum pan and dried in a 65° C. recirculated oven for 12 hours.

Portions of the fabrics were resized in order to evaluate the extensibility characteristics. The fabrics were resized by immersing the material in a 1% aqueous solution of Ultra Downy fabric softener (available from Proctor and Gamble, Cincinnati, Ohio). The initial weight and wet weights are given below in Table 1b.

TABLE 1B

| Run | Dry Weight | Wet Weight |
|---|---|---|
| 1 | 29.05 gm | 41.6 |
| 2 | 24.2 | 36.4 |
| 3 | 43.75 | 64.7 |

The tapes were tested for extensibility (% stretch) under a 22.2N load. The mean values were calculated for several trials (n=3 for Runs 1-3; n=4 for control) and appear in Table 1c.

TABLE 1C

| Run | Wet treatment | Mean % stretch |
|---|---|---|
| Control | none | 25.5 |
| 1 | water | 46.0 |
| 2 | Alconox | 47.8 |
| 3 | Steol CA-460 | 51.8 |

The above data indicates that addition of a detergent helps to achieve greater compaction.

EXAMPLE 2

Integrity of Heat Set Wet Compacted Fabrics:

A portion of the fabric of Run 2 from Example 1 was desized in roll form using the following temperature profile: heat up from 24° C. to 427° C. in 1 hour; hold at 427° C. for 7 hours; and then cool down from 427° C. to 24° C. in 1 hour.

A portion of the sample was then resized as described in Example 1. A control sample of fabric which was not compacted was also heat set and resized. The fabrics were tested for extensibility as described in Example 1. The mean values (% stretch) were calculated for three trials and appear in Table 2a.

TABLE 2A

| Run | Sample | Treatment | Mean |
|---|---|---|---|
| 1 | Control | none | 31.0 |
| 2 | Run 2, Ex. 1 | Alconox/Heat Set | 49.3 |

The integrity of the fabrics was measured by determining their tensile strength. Portions of each fabric (178 mm sections) were first marked off and placed in the standard jaws of an Instron tensile tester Model 1122 having a jaw separation of 178 min. The marks were aligned with the tip of each jaw. The tape was extended at a rate of 127 mm/min until failure. The strain at specific stress levels is given below in Table 2b along with the peak stress (tensile strength) for each fabric. The integrity of the fabric from run 3 of Example 1 which was either resized and not heat set or not resized and not heat set was also determined. The mean values of 5 samples are reported below in Table 2b.

TABLE 2B

| Run | Sample | Treatment Heat Set | Treatment Resized | % Strain at 4.45 N | % Strain at 13.3 N | % Strain at 22.2 N | Tensile Strength (N) |
|---|---|---|---|---|---|---|---|
| 1 | Control | yes | yes | 25.0 | 32.9 | 35.1 | 148.6 |
| 2 | Rn 2, Ex 1 | yes | yes | 41.5 | 53.0 | 56.0 | 66.7 |
| 3 | Rn 3, Ex 1 | no | yes | 40.0 | 51.1 | 53.8 | 71.6 |
| 4 | Rn 3, Ex 1 | no | no | 6.1 | 43.8 | 49.0 | 89.4 |

As is demonstrated in the above table the compacting process has dramatically increased the extensibility of the fabric. Furthermore, the heat setting process was performed without loss of extensibility. Comparing runs 2 and 3 indicates that the heat setting process resulted in only a very minor decrease in the web integrity. Comparing run 1 to runs 2 and 3 appears to indicate that the compacting process results in a decrease in web integrity. This is probably a result of the rather vigorous shaking the samples were subjected to which resulted in visible fiber bundle damage. Less severe vibration such as agitation or ultrasonic vibration should alleviate this problem. Notably, the web integrity is still very high for these samples. It is also worth noting that run 4 which was not resized had a very different stress/strain profile. Without sizing the tape was "stabilized" and pulling out the stretch imparted by the compacting process was difficult. Even at a total load of 4.4N the tape only elongated 6%.

EXAMPLE 3

Ultrasonic Compaction

Two "marks" 152 mm apart were positioned on the center section of a 254 mm long by 76 mm wide piece of the fiberglass fabric of Example 1. The marked tape was immersed for 3 minutes in an ultrasonic cleaner (available from Leco as Model MEII) filled with a 0.75% by weight solution of Alconox in water at 45° C. After this time the 152 mm marked section measured only 139 mm. After an additional 3 minutes in the bath the fabric was removed and rinsed in 45° C. tap water. The marked section now measured only 133 mm (the fabric has been compacted by 12.5%). Since the initial uncompacted fabric had an extensibility of about 25.5% the compacted fabric of this example would have a total extensibility of about 43.4%.

Various modifications and alterations of this invention will be apparent to those skilled in the art without departing from the scope and spirit of this invention, and it should be understood that this invention is not limited to the illustrative embodiments set forth herein.

What is claimed is:

1. An article, comprising:
   a compacted fiberglass knit fabric sheet, wherein said fabric comprises adjacent rows of overlapping yarn loops and
   a curable or hardenable liquid resin coated onto said compacted fabric sheet, wherein said fabric is wet compacted prior to being coated with said curable or hardenable resin by contacting the yarn with a lubricant that allows the loops to stress relax.

2. An article according to claim 1, wherein said lubricant is removed from said fabric sheet and said compacted sheet is heat set prior to being coated with said resin.

3. An article according to claim 1, wherein said lubricant comprises water.

4. An article according to claim 1, wherein said lubricant comprises a reactive functional silane.

5. An article according to claim 1, wherein said lubricant comprises a detergent or surfactant solution.

6. An article according to claim 2, wherein said lubricated fabric is vibrated prior to being heat set.

7. An article according to claim 1, wherein said sheet has from about 25% to about 75% extensibility in the elongated direction when a 2.63N tensile load or force is applied per 1 cm wide section of the fabric.

8. An article according to claim 1, wherein said curable resin is selected from the group consisting of water-curable resins comprising isocyanate-functional prepolymers; water-curable resins comprising a water-reactive liquid organometallic compound and an organic polymer; and alkoxysilane terminated polyurethane prepolymer resins.

9. An article according to claim 3, wherein said fabric has between about 6 and 70 openings per square cm when measured under a 2.63N/cm width tensile force.

10. An article according to claim 1, wherein said fabric was compacted to between about 30 and 90 percent of its original dimension.

11. An article according to claim 1, wherein said fabric was compacted to between about 40 and 80 percent of its original dimension.

12. An article according to claim 8, wherein said resin has a viscosity between about 10 Pa s and 100 Pa s.

13. An article according to claim 2, wherein said lubricated fabric is vibrated prior to being coated with said curable or hardenable resin.

14. A method of making an orthopedic casting bandage, comprising the steps of:
   knitting a high modulus yarn to form a fabric;
   contacting said yarn with a lubricant capable of reducing the coefficient of friction between contacting surfaces of said knit yarn;
   allowing said fabric to stress relax, thereby compacting said fabric; and then
   coating said compacted fabric with a curable or hardenable liquid resin.

15. A method according to claim 14, further comprising the step of:
   heat setting said fabric, and wherein said high modulus yarn comprises fiberglass.

16. A method according to claim 14, wherein said sheet has from about 25% to about 75% extensibility in the elongated direction when a 2.63N tensile load or force is applied per 1 cm wide section of the fabric.

17. A method according to claim 15, wherein said curable resin is selected from the group consisting of water-curable resins comprising isocyanate-functional prepolymers; water-curable resins comprising a water-reactive liquid organometallic compound and an organic polymer; and alkoxysilane terminated polyurethane prepolymer resins.

18. A method according to claim 15, wherein said resin has a viscosity between about 10 Pa s and 100 Pa s, and wherein said fabric is compacted to between about 30 and 80 percent of its original dimension.

19. A method according to claim 14, wherein said lubricant comprises water.

20. A method according to claim 14, wherein said lubricant comprises a detergent or surfactant solution.

21. A method according to claim 14, further comprising the step of:
   vibrating said lubricated yarn; and then allowing said fabric to stress relax.

* * * * *

UNITED STATES PATENT AND TRADEMARK OFFICE
CERTIFICATE OF CORRECTION

PATENT NO.  : 5,370,927
DATED       : December 6, 1994
INVENTOR(S) : Matthew T. Scholz and Jacuelyn A. Schmidt It is certified that error appears in the above-indentified patent and that said Letters Patent is hereby corrected as shown below:

Col. 11, line 45, "east" should read -- cast --.

Col. 11, line 48, "east" should read -- cast --.

Col. 11, line 59, "east" should read -- cast --.

Col. 11, line 67, "an" should read -- art --.

Col. 12, line 17, "hisphenol" should read -- bisphenol --.

Col. 14, lines 24-25, "2-dimethylaminocthyl" should read
    -- 2-dimethylaminoethyl --.

Col. 14, line 51, delete "5".

Col. 15, line 27, "$C_{100}$" should read -- $C_{200}$ --.

Col. 18, line 44, "min." should read -- mm --.

Signed and Sealed this

Fifth Day of September, 1995

Attest:

BRUCE LEHMAN

Attesting Officer

Commissioner of Patents and Trademarks